United States Patent [19]

Karjalainen et al.

[11] Patent Number: 5,292,887

[45] Date of Patent: Mar. 8, 1994

[54] SUBSTITUTED IMIDAZOLE DERIVATIVES AND THEIR PREPARATION AND USE

[75] Inventors: Arto J. Karjalainen, Oulu; Raimo E. Virtanen, Rusko; Arja L. Karjalainen, Oulu, all of Finland

[73] Assignee: Farmos-yhtyma Oy, Turku, Finland

[21] Appl. No.: 446,839

[22] Filed: Dec. 6, 1989

[30] Foreign Application Priority Data

Dec. 9, 1988 [GB] United Kingdom .................. 8828831

[51] Int. Cl.$^5$ ..................... A61K 31/44; C07D 233/54; C07D 233/56
[52] U.S. Cl. ..................................... 514/396; 514/399; 514/400; 514/866; 548/345.1
[58] Field of Search ..................... 548/341, 342, 341.1; 514/399, 400

[56] References Cited

FOREIGN PATENT DOCUMENTS 0183492 6/1986 European Pat. Off. ......... 548/341.1
0247764 12/1987 European Pat. Off. ......... 548/341.1

OTHER PUBLICATIONS

Chemical Abstracts, vol. 109, No. 13, Abstract 104.602h, p. 61, Sep. 26, 1988.

*Primary Examiner*—Dale R. Ore
*Attorney, Agent, or Firm*—Adduci, Mastriani, Schaumberg & Schill

[57] ABSTRACT

Compounds of the formula:

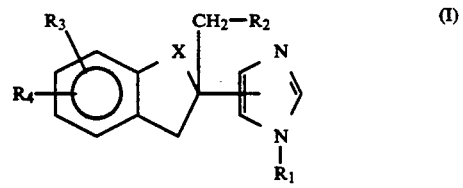

wherein
X is —$CH_2$— or

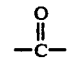

$R_1$ is H, $C_{1-5}$-alkyl or benzyl, which can be substituted or unsubstituted
$R_2$ is H, $C_{1-4}$-alkyl, OH or $C_{1-3}$-alkoxy
$R_3$ is H, $CH_3$, $CH_2CH_3$, $OCH_3$ or Hal
$R_4$ is H, $CH_3$, $CH_2CH_3$, $OCH_3$ or Hal and Hal is halogen and non-toxic acid addition salts and mixtures thereof are highly selective antagonists at postsynaptic $\alpha_2$-adrenoceptors, and are especially useful in the treatment of diabetes.

30 Claims, No Drawings

SUBSTITUTED IMIDAZOLE DERIVATIVES AND THEIR PREPARATION AND USE

The present invention relates to novel 4(5)-substituted imidazole derivatives and their non-toxic salts, and their preparation, to pharmaceutical compositions containing them, and to their use.

The imidazole derivatives of this invention are new potent, selective and long-acting $\alpha_2$-receptor antagonists and have the general formula:

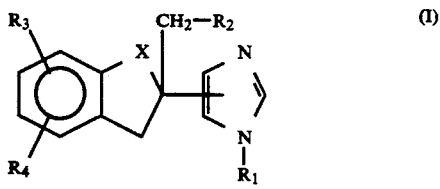

wherein
X is —$CH_2$— or

$R_1$ is H, $C_{1-5}$-alkyl or benzyl, which can be unsubstituted or substituted by e.g., $C_{1-3}$alkyl, $C_{1-3}$alkoxy or halogen, $R_2$ is H, $C_{1-4}$-alkyl, OH or $C_{1-3}$-alkoxy $R_3$ is H, $CH_3$, $CH_2CH_3$, $OCH_3$ or Hal $R_4$ is H, $CH_3$, $CH_2CH_3$, $OCH_3$ or Hal, and Hal is halogen, provided that when $R_2$ is H or $C_{1-3}$-alkyl then $R_1$ cannot be hydrogen and when $R_2$ is OH or $C_{1-3}$-alkoxy then X cannot be CO.

The non-toxic, pharmaceutically acceptable acid addition salts of these compounds are also within the scope of the invention. The compounds of the formula (I) form acid addition salts with both organic and inorganic acids. They can thus form many pharmaceutically usable acid addition salts, as for instance, chlorides, bromides, sulfates, nitrates, phosphates, sulfonates, formates, tartrates, maleates, citrates, benzoates, salicylates, ascorbates and the like.

Valuable $\alpha_2$-adrenoceptor antagonists have been disclosed earlier e.g. in the European patent publications No. 183492 and 247764.

The compounds of this invention are highly selective and longacting antagonists at $\alpha_2$-adrenoceptors and they may be especially valuable in the treatment of diabetes.

$\alpha$-adrenoceptors can be divided on a pharmacological basis into two subclasses, viz $\alpha_1$- and $\alpha_2$-adrenoceptors (see e.g. Starke & Docherty, J. Cardiovasc. Pharmacol., I, Suppl. 1, S14–523, 1981). It is well established that while $\alpha_1$-adrenoceptors are located postsynaptically, $\alpha_2$-adrenoceptors are situated both at presynaptic nerve terminals and postsynaptically e.g. in vascular smooth muscle, platelets, pancreatic $\beta$-cells, fat cells and central nervous system.

The presynaptic $\alpha_2$-receptors modulate the release of noradrenaline by means of a negative feedback mechanism. Thus, if presynaptic $\alpha_2$-adrenoceptors are stimulated (under physiological conditions by noradrenaline) noradrenaline release is inhibited. Blockade of these receptors by an $\alpha_2$-antagonist, on the contrary, increases the release of noradrenaline. $\alpha_2$-adrenoceptor antagonism at presynaptic $\alpha_2$-receptors can thus be expected to be of use in disease states which are believed to be connected with deficiency of noradrenaline available in the postsynaptic adrenoceptors. These diseases include e.g. endogeneous depression.

The best known pharmacodynamic effect mediated by postsynaptic $\alpha_2$-adrenoceptors is the contraction of vascular smooth muscle. Blockade of peripheral postsynaptic $\alpha_2$-adrenoceptors in blood vessels can thus be expected to dilate the vessel and lead to decrease in the blood pressure (Ruffolo et al., J. Cardiovasc. Pharm. 10, 100–103, 1987). $\alpha_2$-blockers may thus be valuable as antihypertensive agents. It is now, however, becoming clear that postsynaptic $\alpha_2$-adrenoceptors have also significance in some other physiological functions.

One of these is the modulation of insulin release from pancreatic Langerhans islets; stimulation of postsynaptically located $\alpha_2$-adrenoceptors in islet $\beta$-cells decreases the amount of insulin released in response to a glucose challenge (Kato & Nakaki, Trends in Pharmacological Sciences 4, 34–36, 1983). Conversely, selective $\alpha_2$-adrenoceptor antagonists are known to be able to increase plasma insulin levels and thus decrease blood glucose levels (Clague et al., Br. J. Pharmacol. 83, 436P, 1984). $\alpha_2$-antagonism in the pancreatic $\beta$-cell can thus be expected to be a potential mechanism for novel antidiabetic agents.

Lipid metabolism in fat cells is also regulated by an inhibitory mechanism involving $\alpha_2$-adrenoceptors. $\alpha_2$-agonists inhibit lipolysis antagonists increase it (Carpene et al., Experientia 36, 1413–1414, 1980). An $\alpha_2$-blocker may thus be of use in obesity.

$\alpha_2$-adrenoceptors also take part in platelet aggregation. It has been shown that $\alpha_2$-agonists activate while antagonists inhibit human platelet aggregation (Grant & Schutter, Nature 277, 659–682, 1979). $\alpha_2$-antagonists may thus be useful in pathogenic states involving increased aggregation, e.g. in migraine.

The present invention resides in the discovery of a group of compounds which exhibit selective and long-acting antagonism at $\alpha_2$-adrenoceptors. This group of compounds has e.g. a potent ability to increase insulin release from pancreas.

In the compounds of formula I the following combination of radicals are preferred:

(i) $R_3$ and $R_4$ are hydrogen, $R_2$ is methyl or methoxy, $R_1$ is methyl, ethyl, n-propyl or benzyl and X is —$CH_2$—;

(ii) $R_3$ and $R_4$ are hydrogen, $R_2$ is OH, $R_1$ is H, methyl or ethyl and X is —$CH_2$—; or (iii) $R_3$ and $R_4$ are hydrogen, $R_2$ is methyl, $R_1$ is methyl or ethyl and X is CO.

Preferred compounds include:
4-(2-ethyl-2,3-dihydro-1H-inden-2-yl)-1-methyl-1H-imidazole
5-(2-ethyl-2,3-dihydro-1H-inden-2-yl)-1-methyl-1H-imidazole
1-ethyl-4-(2-ethyl-2,3-dihydro-1H-inden-2-yl)-1H-imidazole
1-ethyl-5-(2-ethyl-2,3-dihydro-1H-inden-2-yl)-1H-imidazole
4-(2-ethyl-2,3-dihydro-1H-inden-2-yl)-1-n-propyl-1H-imidazole
5-(2-ethyl-2,3-dihydro-1H-inden-2-yl)-1-n-propyl-1H-imidazole
1-benzyl-4-(2-ethyl-2,3-dihydro-1H-inden-2-yl)-1H-imidazole 1-benzyl-5-(2-ethyl-2,3-dihydro-1H-inden-2-yl)-1H-imidazole
2-ethyl-2-(1-methyl-1H-imidazol-4-yl)-1-indanone
2-ethyl-2-(1-methyl-1H-imidazole-5-yl)-1-indanone
[2,3-dihydro-2-(1H-imidazole-4-yl)-1H-inden-2-yl]methanol
[2,3-dihydro-2-(1-methyl-1H-imidazole-4-yl)-1H-inden-2-yl]methanol
4-(2,3-dihydro-2-methoxymethyl-1H-inden-2-yl)-1-methyl-1H-imidazole
[2-(1-benzyl-1H-imidazol-4-yl)-2,3-dihydro-1H-inden-2-yl]methanol
1-benzyl-4-(2,3-dihydro-2-methoxymethyl-1H-inden-2-yl)-1H-imidazole
4-(2,3-dihydro-2-methoxymethyl-1H-inden-2-yl)-1H-imidazole
2-ethyl-2-[1-(4-chlorobenzyl)-1H-imidazol-4-yl]-1-indanone
2-(1-methyl-1H-imidazol-4-yl]-2-n-propyl-1-indanone
2-(1-methyl-1H-imidazol-5-yl]-2-n-propyl-1-indanone
2-(1-ethyl-1H-imidazol-4-yl]-2-n-propyl-1-indanone
2-(1-ethyl-1H-imidazol-5-yl]-2-n-propyl-1-indanone
1-ethyl-4-(2,3-dihydro-2-n-propyl-1H-inden-2-yl)-1H-imidazole
4-(2,3-dihydro-2-n-propyl-1H-inden-2-yl)-1-methyl-1H-imidazole
[2-(1-ethyl-1H-imidazol-4-yl)-2,3-dihydro-1H-inden-2-yl]methanol
1-ethyl-4-(2,3-dihydro-2-methoxymethyl-1H-inden-2-yl)-1H-imidazole
2-ethyl-2-(1-ethyl-1H-imidazol-4-yl)-1-indanone and
their non-toxic, pharmaceutically acceptable salts.

The following compounds of the invention were tested.

TABLE 1

| NO. | Name |
|---|---|
| 1. | 4-(2-ethyl-2,3-dihydro-1H-inden-2-yl)-1-methyl-1H-imidazole |
| 2. | 1-ethyl-4-(2-ethyl-2,3-dihydro-1H-inden-2-yl)-1H-imidazole |
| 3. | 4-(2-ethyl-2,3-dihydro-1H-inden-2-yl)-1-n-propyl-1H-imidazole |
| 4. | 1-benzyl-4-(2-ethyl-2,3-dihydro-1H-inden-2-yl)-1H-imidazole |
| 5. | 2-ethyl-2-(1-methyl-1H-imidazol-4-yl)-1-indanone |
| 6. | [2,3-dihydro-2-(1H-imidazol-4-yl)-1H-inden-2-yl]methanol |
| 7. | 4-(2,3-dihydro-2-methoxymethyl-1H-inden-2-yl)-1-methyl-1H-imidazole |
| 8. | 1-ethyl-4-(2,3-dihydro-2-n-propyl-1H-inden-2-yl)-1H imidazole |
| 9. | 4-(2,3-dihydro-2-n-propyl-1H-inden-2-yl)-1-methyl-1H-imidazole |
| 10. | [2-(1-ethyl-1H-imidazol-4-yl)-2,3-dihydro-1H-inden-2-yl]methanol |
| 11. | 1-ethyl-4-(2,3-dihydro-2-methoxymethyl-1H-inden-2-yl)-1H-imidazole |
| 12. | 2-ethyl-2-(1-ethyl-1H-imidazol-4-yl)-1-indanone |

The pharmacological activity of the compounds of the present invention was determined as follows:

1. $\alpha_2$-adrenoceptor antagonism

It is known that in the rat $\alpha_2$-agonists induce dilatation of the pupil (mydriasis) which effect is transmitted via postsynaptic $\alpha_2$-receptors. In anaesthetized rat, a standard dose of detomidine was administered intravenously. Thereafter increasing doses of the studied antagonist were injected intravenously and the reversal of detomidine-induced mydriasis was followed. The ED50 value of the antagonist, i.e. the dose producing a 50 per cent reversal, was determined. Examples of the results of this test are presented in Table 2.

The duration of the $\alpha_2$-blocking action of the compounds was determined as follows: the antagonists were administered orally at eqvipotent doses to groups of 4 rats 1, 2, 4, 7 or 16 hours before induction of anaesthesia and challenge with cumulative i.v. dosing of detomidine. By calculating the percentage antagonism of the mydriatic effect of 0,1 mg/kg detomidine for each pretreatment group, a time-effect relationship was established. This in turn permitted the measurement of the time taken for the antagonist effect to fall by half. Results are shown in table 2.

2. $\alpha_1$-adrenoceptor antagonism

To obtain information also on the selectivity of the antagonist between $\alpha_1$- and $\alpha_2$-receptors, its ability to inhibit $\alpha_1$-receptors was determined by means of isolated anococcygeus muscle (rat). The reference substances were now phenylephrine, a known $\alpha_1$-agonist, and prazosin, a known $\alpha_1$-antagonist. To determine $\alpha_1$-antagonism, muscular contraction was induced by phenylephrine and the pA$_2$ value of the studied compound was determined (Arunlakshana & Schild, Br. J. Pharmacol. 14, 48–62, 1959). Examples of the results of these tests are also presented in table 2.

TABLE 2

| Comp. No. | $\alpha_1$-antagonism (pA$_2$ vs phenylephrine) | Duration of $\alpha_2$-antagonism (hours) | $\alpha_2$-antagonism (ED50, µg/kg vs detomidine) |
|---|---|---|---|
| 1 | 5.1 | 2.0 | 300 |
| 2 | 5.2 | ND | 200 |
| 3 | 5.2 | ND | 300 |
| 4 | 6.0 | ND | 2000 |
| 5 | <5 | 11.0 | 100 |
| 6 | <5 | ND | 200 |
| 7 | <5 | 7.0 | 300 |
| 8 | <5 | ND | 300 |
| 9 | <5 | ND | 300 |
| 10 | <5 | 7.0 | 300 |
| 11 | <5 | 7.0 | 100 |
| 12 | <5 | 16.0 | 200 |
| atipamezole | <5 | 1.0 | 3.0 |
| idazoxan | 5.3 | <1 | 20 |

ND = not determined

3. Potentiation of insulin release from isolated pancreas

As a further model to study the ability of the compounds of the present invention to block postsynaptic $\alpha_2$-adrenoceptors and further, to demonstrate their possible usefulness in antidiabetic therapy, insulin release from isolated rat pancreas was measured. The pancreas were isolated from Sprague-Dawley rats under anaesthesia and perfused in vitro through its own arterial system with a physiological saline solution containing an appropriate glucose concentration (11 mM) to induce moderate insulin secretion (Hillarire-Buys et al., Eur. J. Pharmacol., 117, 253–257, 1985). Samples for determination of insulin concentration in the perfusate were collected before and during 30 min after adding the studied compounds + glucose. Insulin was measured by a RIA-kit (NOVO). Examples of results from this test are shown in Table 3.

TABLE 3

| | Insulin (ng/ml) in the perfusate | | | | |
|---|---|---|---|---|---|
| Treatment | −5 min | +1 min | +10 min | +20 min | +30 min |
| Control | <0.1 | 5.0 | 2.2 | 3.9 | 7.8 |
| Comp. No. 7 | <0.1 | 26.0 | 11.5 | 15.9 | 22.0 |

TABLE 3-continued

| Treatment | Insulin (ng/ml) in the perfusate | | | | |
|---|---|---|---|---|---|
| | −5 min | +1 min | +10 min | +20 min | +30 min |
| $1 \times 10^{-6}$M atipamezole $1 \times 10^{-6}$M | <0.1 | 5.0 | 3.0 | 6.3 | 15.1 |

The acute toxicity, $LD_{50}$, was determined in rats by oral administration. The $LD_{50}$ value for the compounds is from 100 to 200 mg/kg.

The compounds of this invention react with organic and inorganic acids to form many pharmaceutically usable acid addition salts, as, for instance, chlorides, bromides, sulfates, nitrates, phosphates, sulfonates, formates, tartrates, maleates, citrates, benzoates, salicylates, ascorbates and the like. The salts have the same therapeutic activity as the base.

The compounds and their non-toxic, pharmaceutically acceptable acid addition salts may be administered orally, parenterally or intravenously. In the treatment of diabetes the compounds are preferably administered orally at a daily dose of 0,1 to 10 mg/kg, preferably 1 to 2 mg/kg.

The pharmaceutical carriers which are typically employed with the compound of the invention may be solid or liquid and are generally selected with the planned manner of administration in mind.

The compounds of formula (I) can be prepared according to the following methods:

1. Compounds of formula I in which $R_1$ is hydrogen, $R_2$ is $C_4$-alkyl and X is CO or $CH_2$ can be made by the following method:

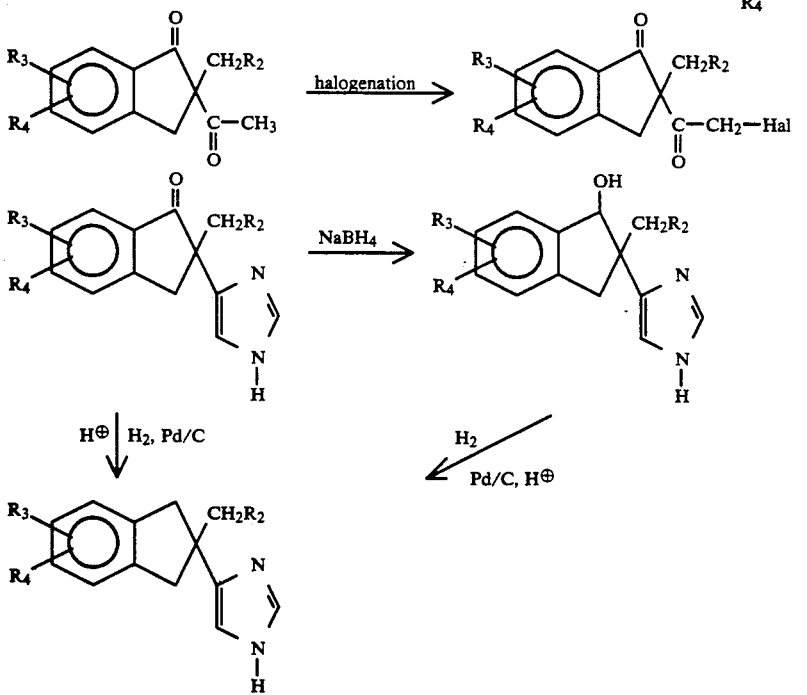

2. Alkylation of nitrogen

The compounds of formula (I) where $R_1$ is other than hydrogen can be synthesized by alkylation of the corresponding compounds where $R_1$ is hydrogen with the alkyl- or arylalkylhalogenide $R_1X$ ($R_1=C_{1-5}$-alkyl or substituted or unsubstituted benzyl; X=halogen) in an appropriate solvent at reaction temperatures varying from room temperature to the boiling point of the solvent.

Solvents which may be used include, for example, toluene, acetonitrile and lower alkyl alcohols. Especially successfully the reaction can be carried out in two phase conditions. Here a favourable combination of solvents is a sodium hydroxide-toluene mixture in the presence of a two phase catalyst such as tetrabutylammonium bromide.

3. Preparation of alcohols

The compounds of formula (I) where $R_2$ is OH and X is $-CH_2-$ can be prepared by reduction of an appropriately substituted indene carboxylate (II)

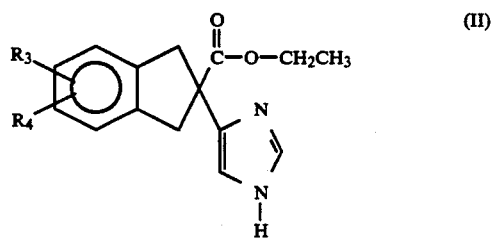

with lithium aluminium hydride to the corresponding alcohol (III)

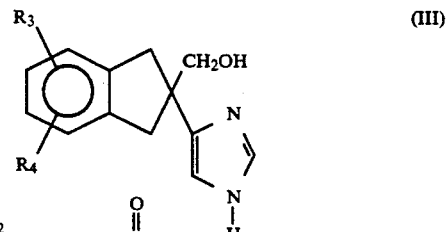

The compound (III) can further be N-alkylated with an alkyl- or arylalkylhalogenide $R_1X$ ($R_1 = C_{1-5}$-alkyl or substituted or unsubstituted benzyl; X=halogen) according to the method described above to give the N-substituted alcohol (IV)

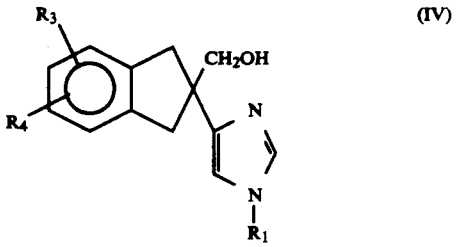

Suitable indene carboxylates of formula II can be prepared using the process of EP-A-247764.

4. Alkylation of oxygen

The compounds of formula (I) where $R_2$ is $C_{1-3}$-alkoxy and X is —$CH_2$— can be prepared by oxygen alkylation of compound (IV) with the alkylhalogenide $R_5X$ ($R_5 = C_{1-3}$-alkyl; X= halogen). The alkylation is performed in the presence of a strong base, for example sodium hydride in tetrahydrofurane to give the corresponding N-substituted ether compounds (V)

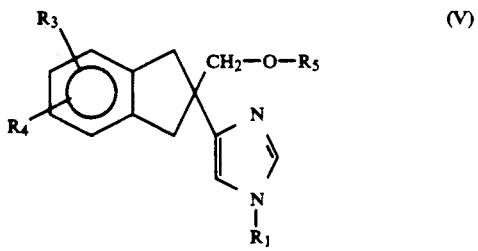

($R_1 = C_{1-5}$-alkyl or substituted or unsubstituted benzyl) Ether compounds of formula (I) where $R_1$ is H can be made from (V) where $R_1$ is a substituted or unsubstituted benzyl by removal of this benzyl group e.g. with sodium in ammonia to give a compound (VI)

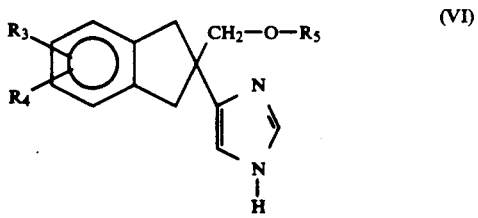

In the examples below, where $^1H$ and $^{13}C$ NMR spectrum shifts are presented, the NMR spectra were determined with a Bruker WB 80 DS spectrometer using tetramethylsilane as the internal reference, from which the presented chemical shifts ($\delta$, ppm) were measured downfield. The letters s, d, t and m are used to indicate a singlet, doublet, triplet or multiplet, respectively. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide or deuterium methanol. The mass spectra were determined with a Kratos MS 80 RF Autoconsole apparatus.

EXAMPLE 1

4-(2-ethyl-2,3-dihydro-1H-inden-2-yl)-1-methyl-1H-imidazole 1,0 g of 4-(2-ethyl-2,3-dihydro-1H-inden-2-yl)-1H-imidazole (preparation disclosed in GB 2167408), 4 ml of 48% NaOH, 10 ml of toluene and 0,075 g of tetrabutylammonium bromide were mixed while stirring. Finally 1,15 g of methyl iodide in 3 ml of toluene were added. After the addition the mixture was warmed to +40° C. The reaction mixture was stirred at this temperature for 1 h after which the reaction mixture was cooled. Water was added to the mixture and the the product was washed extracted in toluene. The toluene solution was washed with water and evaporated and 1 g of product (94%) was obtained.

The crude product was purified by flash chromatography (eluent methylene chloride-methanol 5,5:0,5). The hydrochloride of the product (oil) was prepared in ethyl acetate.

MS: 226 (27, M+.), 211 (10, M-$CH_3$), 197 (M-$CH_2CH_3$)

HCl-salt, $^1H$ NMR (80 MHz, MeOH-$d_4$): $\delta$0.82 (3H, t, J=7.4 Hz, $CH_2CH_3$), 1.92 (2H, q, J=7.4 Hz, $CH_2CH_3$), 3.18 and 3.25 (4H, AB q, $J_{AB}$=16.5 Hz, indane ring $H_2^1$ and $H_2^3$), 3.87 (3H, s, >$NCH_3$), 7.05-7.30 (4H, m, arom.), 7.39 (1H, d, J=1.5 Hz, im-5), 8.85 (1H, d, J=1.5 Hz, im-2)

HCl-salt, $^{13}C$ NMR (20 MHz, MeOH-$d_4$): $\delta$9.84 (OFR q), 33.33 (t), 36.27 (q), 44.65 (2t), 48.47 (s), 121.18 (d), 125.45 (2d), 127.75 (2d), 136.74 (d), 141.80 (s), 142.04 (2s)

EXAMPLE 2

1-ethyl-4- and 5-(2-ethyl-2,3-dihydro-1H-inden-2-yl)-1H-imidazole

The alkylation of 4-(2-ethyl-2,3-dihydro-1H-inden-2-yl)-1H-imidazole was performed according to example 1 except that ethyl iodide was used. The crude yield of the products was 91%. Separation of the isomers were performed by flash chromatography. The hydrochloride of the products were prepared in ethyl acetate.

1-ethyl-4-(2-ethyl-2,3-dihydro-1H-inden-2-yl)-1H-imidazole:

M.P. of the hydrochloride was 206°-208° C.

MS: 240 (30, M+.), 225 (12, M-$CH_3$), 211 (100, M-$CH_2CH_3$), 129 (10), 115 (21)

HCl-salt, $^1H$ NMR (80 MHz, MeOH-$d_4$): $\delta$0.81 (3H, t, J=7.5 Hz, $CH_2CH_3$), 1.49 (3H, t, J=7.4 Hz, >$NCH_2CH_3$), 1.91 (2H, q, J=7.5 Hz, $CH_2CH_3$), 3.16 and 3.27 (4H, AB q, $J_{AB}$=16.6 Hz, indane ring $H_2^1$ and $H_2^3$), 4.20 (2H, q, J=7.4 Hz, >$NCH_2CH_3$), 7.05-7.30 (4H, m, arom.), 7.49 (1H, d, J=1.5 Hz, im-5), 8.91 (1H, d, J=1.5 Hz, im-2)

1-ethyl-5-(2-ethyl-2,3-dihydro-1H-inden-2-yl)-1H-imidazole:

MS: 240 (34, M+.), 225 (14, M-$CH_3$), 211 (100, M-$CH_2CH_3$), 182 (17, 211-$CH_2CH_3$), 181 (10), 170 (10), 156 (10), 154 (12), 129 (25), 128 (29), 127 (20), 115 (40), 91 (12), 77 (14)

HCl-salt, $^1H$ NMR (80 MHz, MeOH-d4): $\delta$0.75 (3H, t, J=7.4 Hz, $CH_2CH_3$), 1.63 (3H, t, J=7.2 Hz, >$NCH_2CH_3$), 1.88 (2H, q, J=7.4 Hz, $CH_2CH_3$), the middle of the AB quartet ca. 3.3 ppm (4H, $H_2^1$ and $H_2^3$ of the indane ring), 4.39 (2H, q, J=7.2 Hz, >$NCH_2CH_3$), 7.05-7.33 (4H, m, arom.), 7.41 (1H, d, J=1.7 Hz, im-4), 9.00 (1H, d, J=1.7 Hz, im-2)

EXAMPLE 3

4-(2-ethyl-2,3-dihydro-1H-inden-2-yl)-1-n-propyl-1H-imidazole

The alkylation of 4-(2-ethyl-2,3-dihydro-1H-inden-2-yl)-1H-imidazole was performed according to example 1 except that n-propyl iodide was used. The yield was 86%. The main isomer was separated by flash chromatography and the hydrochloride was prepared in ethyl acetate.

M.p. of the hydrochloride was 218°-220° C.

MS: 254 (26, M+.) 239 (11, M-CH$_3$), 225 (100, M-CH$_2$CH$_3$), 183 (18), 182 (10), 136 (16), 129 (12), 128 (13), 127 (10), 115 (21)

HCl-salt, $^1$H NMR (80 MHz, MeOH-d$_4$): δ0.81 (3H, t, CH$_2$CH$_3$), 0.91 (3H, t, CH$_2$CH$_2$CH$_3$), 1.68-2.13 (4H, m, CH$_2$CH$_3$ and CH$_2$CH$_2$CH$_3$), 3.18 and 3.27 (4H, AB q, $J_{AB}$=16.5 Hz, indane ring H$_2^1$ and H$_2^3$), 4.13 (2H, t, J=7.1 Hz, >NCH$_2$CH$_2$—), 7.05-7.30 (4H, m, arom.), 7.48 (1H, d, J=1.5 Hz, im-5), 8.92 (1H, d, J=1.5 Hz, im-2)

EXAMPLE 4

1-benzyl-4-(2-ethyl-2,3-dihydro-1H-inden-2-yl)-1H-imidazole

The benzylation of 4-(2-ethyl-2,3-dihydro-1H-inden-2-yl)-1H-imidazole was performed according to example 1 by benzylation with benzyl chloride. The yield was 100%. The hydrochloride was prepared in ethyl acetate.

M.p. of the hydrochloride was 158°-161° C.

MS: 302 (37, M+.), 287 (8, M-CH$_3$), 273 (83, M-CH$_2$CH$_3$), 182 (23, M-CH$_2$Ph), 128 (10), 115 (10), 91 (100, C$_7$H$_7$+)

HCl-salt, $^1$H NMR (80 MHz, MeOH-d$_4$): δ0.78 (3H, t, J=7.4 Hz, CH$_3$), 1.89 (2H, q, J=7.4 Hz, CH$_2$CH$_3$), 3.16 and 3.24 (4H, AB q, $J_{AB}$=16.4 Hz, indane ring H$_2^1$ and H$_2^3$), 5.36 (2H, s, CH$_2$Ph), 7.04-7.28 (4H, m, the aromatic protons of the indane ring), 7.38 (5H, s, the protons of the benzene ring), 7.44 (1H, d, J=1.5 Hz, im-5), 9.00 (1H, d, J=1.5 Hz, im-2)

EXAMPLE 5

2-ethyl-2-(1-methyl-1H-imidazol-4- and 5-yl)-1-indanone)

20 ml of toluene, 8 ml of 48% NaOH, 0,10 g of tetrabutylammonium bromide and 1,5 g of 2-ethyl-2-(1H-imidazol-4-yl)-1-indanone (prepared according to EP 183492) were added to a flask. The mixture was warmed to +40° C. 1,4 g of methyl iodide were added dropwise to the reaction mixture while stirring carefully and stirring was continued for 1 h at +40° C. Then the reaction mixture was cooled and water was added. The product was extracted in toluene, the toluene solution was washed with water and evaporated. The products were separated and purified flash chromatographically (eluent methylene chloride - methanol 9,5:0,5). The hydrochloride (oil) was prepared in ethyl acetate.

2-ethyl-2-(1-methyl-1H-imidazol-4-yl)-1-indanone:

MS: 240 (32, M+.), 225 (15, M-CH$_3$), 211 (100, M-CH$_2$CH$_3$), 115 (13)

HCl-salt, $^1$H NMR (80 MHz, MeOH-d$_4$): δ0.85 (3H, distorted t, CH$_2$CH$_3$), 1.71-2.28 (2H, m, CH$_2$CH$_3$), 3.57 (2H, the middle of the AB quartet, indane ring CH$_2$), 3.95 (3H, s, >NCH$_3$), 7.37-7.88 (5H, m, arom. and im-5), 8.97 (1H, broad s, im-2)

2-ethyl-2-(1-methyl-1H-imidazol-5-yl)-1-indanone:

HCl-salt, $^1$H NMR (80 MHz, MeOH-d$_4$): δ0.80 (3H, distorted t, CH$_2$CH$_3$), 1.8-2.3 (2H, m, CH$_2$CH$_3$), 3.6 (2H, m, the indane ring CH$_2$), 3.77 (3H, s, >NCH$_3$), 7.4-7.9 (5H, m, arom. and im-5), 8.9 (1H, broad s, im-2)

EXAMPLE 6

2-ethyl-2-[1-(4-chlorobenzyl)-1H-imidazol-4-yl]-1-indanone 2-ethyl-2-(1H-imidazol-4-yl)-1-indanone and 4-chlorobenzyl chloride were reacted at 60° C. as described in example 5. The yield was 74%. The hydrochloride was prepared in ethyl acetate, m.p. 150°-154° C.

MS: 350 and 352 (26 and 9, M+.), 321 and 323 (51 and 17, M-CH$_2$CH$_3$), 225 (8, M-CH$_2$C$_6$H$_4$Cl), 196 (10, 321-CH$_2$C$_6$H$_4$Cl), 125 and 127 (100 and 35, CH$_2$C$_6$H$_4$Cl), 91 (16), 89 (12)

HCl-salt, $^1$H NMR (MeOH-d$_4$): δ0.82 (3H, distorted t, CH$_3$), 1.78-2.26 (2H, m, —CH$_2$CH$_3$), 3.50 and 3.57 (2H, AB q, $J_{AB}$=18.0 Hz, indane ring H$_2^3$), 5.42 (2H, s, >NCH$_2$—), 7.31-7.91 (9H, m, arom. and im-5), 9.09 (1H, d, J=1.5 Hz)

HCl-salt, $^{13}$C NMR (MeOH-d$_4$): δ9.23 (OFR q), 32.42 (t), 38.45 (t), 53.22 (t or s), 53.28 (s or t), 120.45 (d), 125.42 (d), 127.93 (d), 129.32 (d), 130.35 (2d), 131.23 (2d), 134.02 (s), 135.38 (s), 136.14 (s), 136.71 (s), 137.16 (d), 137.26 (d), 153.63 (s), 205.73 (s)

EXAMPLE 7

2-(1-methyl-1H-imidazol-4- and 5-yl)-2-n-propyl-1-indanone 2-(1H-imidazol-4-yl)-2-n-propyl-1-indanone (prepared according to EP 183492) and methyl iodide were reacted as described in example 5. The yield was 80%. The isomers were separated by flash chromatography (eluent methylene chloride - methanol 9,5:0,5). The hydrochloride salts of the isomers were prepared in ethyl acetate.

2-(1-methyl-1H-imidazol-4-yl)-2-n-propyl-1-indanone:

The hydrochloride was an oil.

HCl-salt, $^1$H NMR (80 MHz, MeOH-d$_4$): δ0.89 (3H, distorted t, —CH$_2$CH$_3$), 1.02-1.44 (2H, m, CH$_2$CH$_2$CH$_3$), 1.68-2.28 (2H, m, CH$_2$CH$_2$CH$_3$), 3.57 (2H broad s, indane ring CH$_2$), 3.93 (3H, s, >NCH$_3$), 7.37-7.87 (5H, m, arom. and im-5), 8.93 (1H, broad s, im-2)

HCl-salt, $^{13}$C NMR (20 MHz, MeOH-d$_4$): δ14.38 (OFR q), 18.95 (t), 36.51 (q), 38.90 (t), 41.32 (t), 52.80 (s), 121.45 (d), 125.27 (d), 127.87 (d), 129.20 (d), 135.17 (s), 136.04 (s), 137.10 (d), 137.38 (d), 153.48 (s), 205.58 (s)

2-(1-methyl-1H-imidazol-5-yl)-2-n-propyl-1-indanone:

MS: 254 (32, M+.), 225 (48, M-CH$_2$CH$_3$), 211 (100, M-CH$_2$CH$_2$CH$_3$), 183 (10), 115 (14), 98 (11), 42 (19)

EXAMPLE 8

2-(1-ethyl-1H-imidazol-4- and 5-yl)-2-n-propyl-1-indanone 2-(1H-imidazol-4-yl)-2-n-propyl-1-indanone (prepared according to EP 183492) and ethyl iodide were reacted as described in example 5. The yield was 98%. The isomers were separated by flash chromatography (eluent methylene chloride-methanol 9,5:0,5). The hydrochloride salts of the isomers were prepared in ethyl acetate.

2-(1-ethyl-1H-imidazol-4-yl)-2-n-propyl-1-indanone:

M.p. of the hydrochloride 180°-194° C.

HCl-salt, ¹H NMR (80 MHz, MeOH-d₄): δ0.90 (3H, distorted t, —CH₂CH₂C$\underline{H}_3$), ca. 1.0-1.4 (2H, m, CH₂C$\underline{H}_2$CH₃), 1.52 (3H, t, J=7.4 Hz, >NCH₂C$\underline{H}_3$), 1.68-2.28 (2H, m, —C$\underline{H}_2$CH₂CH₃), 3.54 and 3.61 (2H, AB q, J$_{AB}$=17.8 Hz, indane ring CH₂), 4.26 (2H, q, J=7.4 Hz, >NC$\underline{H}_2$CH₃), 7.37-7.87 (5H, m, arom. and im-5), 8.98 (1H, $\overline{d}$, J=1.5 Hz, im-2)

HCl-salt, ¹³C NMR (20 MHz, MeOH-d₄): δ14.41 (OFR q), 15.56 (q), 19.07 (t), 38.87 (t), 41.44 (t), 45.98 (t), 52.98 (s), 120.00 (d), 125.42 (d), 127.96 (d), 129.32 (d), 135.35 (s), 136.47 (d and s), 137.23 (d), 153.66 (s), 205.76 (s)

2-(1-ethyl-1H-imidazol-5-yl)-2-n-propyl-1-indanone:
MS: 268 (28, M⁺.), 239 (36, M-CH₂CH₃), 225 (100, M-CH₂CH₂CH₃), 197 (16).

EXAMPLE 9

4-(2,3-dihydro-2-methoxymethyl-1H-inden-2-yl)-1-methyl-1H-imidazole a) [2,3-dihydro-2-(1H-imidazol-4-yl)-1H-inden-2-yl]methanol 2,8 g of LiAlH₄ were added to 75 ml of dry tetrahydrofurane in nitrogen atmosphere. 15,0 g of ethyl 2,3-dihydro-2-(1H-imidazol-4-yl)-1H-indene-2-carboxylate (prepared according to EP 247764) were dissolved in 150 ml of dry THF and slowly added dropwise at room temperature. After the addition the mixture was stirred for 2 h at room temperature and then for an additional 2 h at +40° C. Excess of LiAlH₄ was decomposed by slow addition of ethyl acetate. Then the mixture was poured into dilute hydrochloric acid. The aqueous solution was washed with methylene chloride and made alkaline with sodium hydroxide. The product was extracted in ethyl acetate. The precipitate formed during the extraction was filtered and washed several times with hot ethyl acetate and methylene chloride. The organic solutions were combined, dried and evaporated. The hydrochloride of the product was made in ethyl acetate by HCl-ethyl acetate, m.p. 181°-184° C.

MS: 214 (18, M⁺.), 196 (10, M-H₂O), 195 (14), 183 (100, M-CH₂OH), 175 (19), 162 (46), 145 (10), 133 (13), 129 (13), 128 (10), 121 (14), 120 (18), 115 (24), 91 (27), 77 (16)

HCl-salt, ¹H NMR (80 MHz, MeOH-d₄): δ3.24 and 3.28 (4H, AB q, J$_{AB}$=16.2 Hz, indane ring H₂¹ and H₂³), 3.68 (2H, s, C$\underline{H}_2$OH), 7.08-7.32 (4H, m, arom.), 7.40 (1H, d, J=1.4 Hz, im-5(4)), 8.81 (1H, d, J=1.4 Hz, im-2)

b) [2,3-dihydro-2-(1-methyl-1H-imidazol-4-yl)-1H-inden-2-yl]-methanol

Tetrabutylammonium bromide (0,51 g) and 48% NaOH-solution (26 ml) were mixed. 68 ml of toluene and 6,8 g of [2,3-dihydro-2-(1H-imidazol-4-yl)-1H-inden-2-yl]methanol as base were added and the mixture was warmed to 40° C.

6,4 g of methyl iodide were added dropwise and the mixture was stirred for 3 h at +40° C. Then the reacation mixture was cooled, water was added and the toluene layer was removed. The aqueous layer was extracted with toluene. The combined toluene solutions were washed with water, dried and evaporated. The product (base) was crystallized from acetone, m.p. 103°-106° C. The hydrochloride was prepared in isopropanol-ethyl acetate, m.p. 224°-229° C.

MS: 228 (17, M⁺.), 197 (100, M-CH₂OH), 115 (13), 98 (16)

HCl-salt, ¹H NMR (80 MHz, MeOH-d₄): δ3.22 and 3.27 (4H, AB q, J$_{AB}$=16.4 Hz, indane ring H₂¹ and H₂³), 3.67 (2H, s, C$\underline{H}_2$OH), 3.89 (3H, s, CH₃), 7.07-7.33 (4H, m, arom.), $\overline{7.43}$ (1H, d, J=1.5 Hz, im-5), 8.79 (1H, d, J=1.5 Hz, im-2)

c) 4-(2,3-dihydro-2-methoxymethyl-1H-inden-2-yl)-1-methyl-1H-imidazole

Sodium hydride (0,89 g of a 50% NaH-mineral oil dispersion washed with pentane) and 10 ml of dry tetrahydrofurane were added to a flask in nitrogen atmosphere. The suspension was warmed to 45°-50° C. and 1,38 g of [2,3-dihydro-2-(1-methyl-1H-imidazol-4-yl)-1H-inden-2-yl]methanol in 4 ml of THF and 1,42 g of methyl iodide were added dropwise at this temperature. After the addition the mixture was stirred for 40 min at 45° C. Then the mixture was cooled and water was added very carefully. THF was evaporated and the mixture was acidified with concentrated hydrochloric adic during simultaneous cooling. Then the mixture was washed with ether, the aqueous solution was made alkaline and the product was extracted in ethyl acetate. The yield was 1,24 g (85%). The hydrochloride was prepered in isopropanol-ethyl acetate, m.p. 177°-180° C.

MS: 242 (14, M⁺.), 211 (10, M-OCH₃), 197 (100, M-CH₂OCH₃), 115 (14)

HCl-salt, ¹H NMR (80 MHz, MeOH-d₄), δ3.26 (4H, s, indane ring H₂¹ and H₂³), 3.33 (3H, s, OCH₃), 3.54 (2H, s, —CH₂O—), 3.88 (3H, s, >NCH₃), 7.07-7.32 (4H, m, arom.), 7.42 (1H, d, J=1.5 Hz, im-5), 8.80 (1H, d, J=1.5 Hz, im-2)

HCl-salt, ¹³C NMR (20 MHz, MeOH-d₄): δ36.24 (OFR q), 42.26 (2t), 48.07 (s), 59.52 (q), 78.68 (t), 120.91 (d), 125.66 (2d), 127.96 (2d), 136.50 (d), 140.74 (s), 141.52 (2s)

EXAMPLE 10

4-(2,3-dihydro-2-methoxymethyl-1H-inden-2-yl)-1H-imidazole a) [2-(1-benzyl-1H-imidazol-4-yl)-2,3-dihydro-1H-inden-2-yl]-methanol 0,0237 g of tetrabutylammonium bromide, 1 ml of 48% NaOH, 5 ml of toluene, 0,58 g of [2,3-dihydro-2-(1H-imidazol-4-yl)-1H-inden-2-yl]methanol hydrochloride prepared according to example 9a and 0,30 g of benzyl chloride were combined. The mixture was stirred for 2 h at 60°-70° C. Then the mixture was cooled and water was added, toluene was evaporated and the aqueous solution was made acidic while cooling simultaneously. The acid solutation was washed with ether and the product separated as an oily layer. The product was extracted in methylene chloride as hydrochloride.

HCl-salt, ¹H NMR (80 MHz, MeOH-d₄): δ3.23 (4H, s, indane ring H₂¹ and H₂³), 3.65 (2H, s, —CH₂O—), 5.38 (2H, s, C$\underline{H}_2$Ph), 6.99-7.30 (4H, m, indane ring H-4, H-5, H-6 and $\overline{H}$-7), 7.41 (5H, s, CH₂C₆H₅), 7.49 (1H, d, J=1.5 Hz, im-5), 8.96 (1H, d, J=1.5 $\overline{Hz}$, im-2)

b) 1-benzyl-4-(2,3-dihydro-2-methoxymethyl-1H-inden-2-yl)-1H-imidazole

The reaction was performed according to example 9c using 1,66 g of [2-(1-benzyl-1H-imidazol-4-yl)-2,3-dihydro-1H-inden-2-yl]methanol (base) and 1,42 g of methyl iodide as starting materials, sodium hydride (0,84 g of a 50% dispersion of NaH in mineral oil) as reagent and dry tetrahydrofuran as solvent.

When the reaction was completed, the mixture was carefully poured in water, THF was evaporated and the product was extracted in ethyl acetate. The yield was 89%. The hydrochloride was prepared in ethyl acetate, m.p. 159°-163° C.

MS: 318 (18, M+.), 287 (10, M-OCH₃), 273 (87, M-CH₂OCH₃), 182 (12, 273-CH₂Ph), 91 (100, C₇H₇+)

HCl-salt, ¹H NMR (80 MHz, MeOH-d₄): δ3.24 (4H, s, the indane ring H₂¹ and H₂³), 3.31 (3H, s, CH₃), 3.50 (2H, s, —CH₂O—), 5.37 (2H, s, CH₂Ph), 7.18 (4H, s, the indane ring H-4, H-5, H-6 and H-7), 7.40 (5H, s, CH₂C₆H₅), 7.47 (1H, d, J=1.5 Hz, im-5), 8.93 (1H, d, J=1.5 Hz, im-2)

c) 4-(2,3-dihydro-2-methoxymethyl-1H-inden-2-yl)-1H-imidazole 2,00 g of 1-benzyl-4-(2,3-dihydro-2-methoxymethyl-1H-inden-2-yl)-1H-imidazole were dissolved in 20 ml of toluene. The solution was cooled to −40° C. and about 20 ml of liquid ammonia were added. Then metallic sodium was added in small portions until the blue color lasted for a while. According to thin layer chromatography the reaction was completed. Solid ammonium chloride was added, ammonia was allowed to evaporate and ethanol and water were added. After evaporation of the solvents water was again added and the solution was acidified with concentrated hydrochloric acid. The aqueous solution was washed with LIAV and then it was made alkaline. The product was extracted in toluene (yield 96%) and crystallized from ethyl acetate, m.p. 153°-157° C. The hydrochloride was prepared in ethyl acetate, m.p. 96°-101° C.

MS: 228 (22, M+.), 195 (12), 183 (100, M-CH₂OCH₃), 129 (11), 115 (17)

Base ¹H NMR (80 MHz, CDCl₃): δ3.21 (4H, s, indane ring H₂¹ and H₂³), 3.35 (3H, s, CH₃), 3.55 (2H, s, —CH₂O—), 6.81 (1H, broad s, im-5), 7.17 (4H, s, arom.), 7.54 (1H, broad s, im-2)

HCl-salt, ¹H NMR (80 MHz, MeOH-d₄): δ3.28 (4H, s, the indane ring H₂¹ and H₂³), 3.34 (3H, s, CH₃), 3.54 (2H, s, —CH₂—), 7.08-7.32 (4H, s, arom.), 7.39 (1H, d, J=1.5 Hz, im-5). 8.80 (1H, J=1,5 Hz, im-2).

EXAMPLE 11

4-(2,3-dihydro-2-n-propyl-1H-inden-2-yl)-1-methyl-1H-imidazole

The N-methylation of 4-(2,3-dihydro-2-n-propyl-1H-inden-2-yl)-1H-imidazole (preparation disclosed in GB 2167408) was performed according to Example 1. The crude product was purified by flash chromatography (eluent methylene chloride-methanol 9.5:0.5).

M.p. of the hydrochloride was 84°-86° C.

MS: 240(28, M+.), 211 (18, M-CH₂CH₃), 197 (100, M-CH₂CH₂CH₃), 115 (16), 98 (22)

HCl-salt, ¹H NMR (80 MHz, MeOH-d₄): δ0.75-1.36 (5H, m, CH₂CH₃), 1.78-2.01 (2H, m, CH₂CH₂CH₃), 3.22 (4H, AB q, the indane ring H₂¹ and H₂³), 3.85 (3H, s, >NCH₃), 7.04-7.29 (4H, m, arom.), 7.35 (1H, d, J=1.5 Hz, im-5), 8.80 (1H, broad s, im-2)

EXAMPLE 12

1-ethyl-4- and 5-(2,3-dihydro-2-n-propyl-1H-inden-2-yl)-1H-imidazole

The N-ethylation of 4-(2,3-dihydro-2-n-propyl-1H-inden-2-yl)-1H-imidazole was performed according to example 2. The reaction temperature was 40°-60° C. The crude yield of the product was 94%.

1-ethyl-4-(2,3-dihydro-2-n-propyl-1H-inden-2-yl)-1H-imidazole:

M.p. of the hydrochloride was 205°-207° C.

MS: 254(25, M+.), 225(16, M-CH₂CH₃), 211(100, M-CH₂CH₂CH₃), 115(10).

HCl-salt, ¹H NMR (80 MHz, MeOH-d₄): δ0.79-1.44 (5H, m, CH₂CH₂CH₃), 1.49 (3H, t, J=7.4 Hz, >NCH₂CH₃), 1.77-2.00 (2H, m, CH₂CH₂CH₃), 3.18 and 3.27 (4H, AB q, J_{AB}=16.0 Hz, the indane ring H₂¹ and H₂²), 4.21 (2H, q, J=7.4 Hz, >NCH₂CH₃), 7.04-7.29(4H, m, arom.), 7.48 (1H, d, J=1.5 Hz, im-5), 8.92 (1H, broad s, im-2)

1-ethyl-5-(2,3-dihydro-2-n-propyl-1H-inden-2-yl)-1H-imidazole:

MS: 254(32, M+.), 211(100, M-CH₂CH₂CH₃), 115(13)

EXAMPLE 13

2-ethyl-2-(1-ethyl-1H-imidazol-4- and 5-yl)-1-indanone

The N-ethylation of 2-ethyl-2-(1H-imidazol-4-yl)-1-indanone was performed according to example 5 except that ethyl iodide was used. The reaction temperature was 60° C. and the reaction time 2 hours. The total yield of the products (the mixture of the isomers) was 98%. The crystallization of the mixture of the isomers from petroleum ether afforded pure 2-ethyl-2-(1-ethyl-1H-imidazol-4-yl)-1-indanone. The 1,5-isomer was separated by flash chromatography (eluent methylene chloride-methanol 9.5:0.5)

2-ethyl-2-(1-ethyl-1H-imidazol-4-yl)-1-indanone:

M.p. of the base was 85°-88° C.

MS: 254 (28, M+.), 239 (16, M-CH₃), 225 (100, M-CH₂CH₃)

Base, ¹H NMR (300 MHz, CDCl₃): δ0.85 (3H, t, J=7.5 Hz, CH₂CH₃), 1.41 (3H, t, J=7.4 Hz, >NCH₂CH₃), 2.02 (2H, q, J=7.5 Hz, CH₂CH₃), 3.29 and 3.90 (2H, AB q, J_{AB}=17.6 Hz, the indane ring H₂³), 3.90 (2H, q, J=7.4 Hz, >NCH₂CH₃), 6.94 (1H, d, J=1.3 Hz, im-5), 7.36 (1H, d, J=1.3 Hz, im-5), 7.32-7.77 (4H, m, arom.)

2-ethyl-2-(1-ethyl-1H-imidazol-5-yl)-1-indanone:

MS: 254(23, M+.), 225(100, M-CH₂CH₃), 197(17), 115(11)

EXAMPLE 14

1-ethyl-4-(2,3-dihydro-2-methoxymethyl-1H-inden-2-yl)-1H-imidazole a) [2-(1-ethyl-1H-imidazol-4-yl)-2,3-dihydro-1H-inden-2-yl]methanol The N-ethylation of [2,3-dihydro-2-(1H-imidazol-4-yl)-1H-inden-2-yl]methanol was performed according to example 9b except that ethyl iodide was used. The reaction temperature was 40°-60° C. The crude product (base) was purified by flash chromatography (eluent methylene chloride-methanol 9.5:0.5). The yield was 93%. The hydrochloride was prepared in ethyl acetate, m.p. 162°-165° C.

MS: 242 (25, M+.), 211 (100, M-CH₂OH), 182 (12, 211-CH₂CH₃), 129 (10), 128 (10), 127 (10), 115 (21).

HCl-salt, ¹H NMR (80 MHz, MeOH-d₄): δ1.52(3H, t, J=7.4 Hz, CH₃), 3.23 and 3.27 (4H, AB q, J_{AB}=16.4 Hz, the indane ring H₂¹ and H₂³), 3.67 (2H, s, —CH₂O—), 4.24 (2H, q, J=7.4 Hz, —CH₂CH₃), 7.08-7.32 (4H, m, arom.), 7.54 (1H, d, J=1.6 Hz, im-5), 8.89 (1H, d, J=1.6 Hz, im-2)

HCl-salt, ¹³C NMR (20 MHz, MeOH-d₄): δ15.56 (OFR q), 41.75 (2t), 45.77 (t), 49.28 (s), 68.11 (t), 119.49 (d), 125.69 (2d), 127.90 (2d), 135.44 (d), 141.07 (s), 141.71 (2s).

b) 1-ethyl-4-(2,3-dihydro-2-methoxymethyl-1H-inden-2-yl)-1H-imidazole 1-ethyl-4-(2,3-dihydro-2-methoxymethyl-1H-inden-2-yl)-1H-imidazole was produced using the method according to example 9c. The yield was 83%. The hydrochloride was prepared in ethyl acetate, m.p. 172°–174° C.

MS: 256 (16, M+.), 225 (10, M-OCH$_3$), 211 (100, M-CH$_2$OCH$_3$), 115 (14)

HCl-salt, $^1$H NMR (80 MHz, MeOH-d$_4$): δ1.51 (3H, t, J=7.4 Hz, CH$_2$CH$_3$), 3.27 (4H, s, indane ring H$_2$$^1$ and H$_2$$^3$), 3.33 (3H, s, CH$_2$OCH$_3$), 3.53 (2H, s, CH$_2$OCH$_3$), 4.23 (2H, q, J=7.4 Hz, CH$_2$CH$_3$), 7.06–7.32 (4H, m, arom.), 7.53 (1H, d, J=1.5 Hz, im-5), 8.88 (1H, d, J=1.5 Hz, im-2)

We claim:

1. A compound which is a substituted imidazole of the formula:

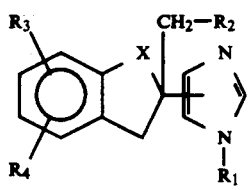

or non-toxic, pharmaceutically acceptable salt thereof wherein

X is —CH$_2$— or

R$_1$ is H, C$_{1-5}$-alkyl or benzyl, which can be or unsubstituted or substituted by C$_{1-3}$ alkyl, C$_{1-3}$ alkoxy or halogen R$_2$ is H, C$_{1-4}$-alkyl, OH or C$_{1-3}$-alkoxy R$_3$ is H, CH$_3$, CH$_2$CH$_3$, OCH$_3$ or Hal R$_4$ is H, CH$_3$, CH$_2$CH$_3$, OCH$_3$ or Hal provided that when R$_2$ is H, OH or C$_{1-4}$-alkyl then R$_1$ cannot be hydrogen and when R$_2$ is OH or C$_{1-3}$-alkoxy then X cannot be CO.

2. A compound according to claim 1 where R$_3$ and R$_4$ are hydrogen, R$_2$ is methyl or methoxy and R$_1$ is methyl, ethyl, n-propyl or benzyl and X is —CH$_2$—.

3. A compound according to claim 1 where R$_3$ and R$_4$ are hydrogen, R$_2$ is methyl, R$_1$ is methyl or ethyl and X is CO.

4. A compound according to claim 1 4-(2-ethyl-2,3-dihydro-1H-inden-2-yl)-1-methyl-1H-imidazole or a non-toxic, pharmaceutically acceptable salts.

5. A compound according to claim 1 5-(2-ethyl-2,3-dihydro-1H-inden-2-yl)-1-methyl-1H-imidazole or a non-toxic, pharmaceutically acceptable salts.

6. A compound according to claim 1 1-ethyl-4-(2-ethyl-2,3-dihydro-1H-inden-2-yl)-1H-imidazole or a non-toxic, pharmaceutically acceptable salts.

7. A compound according to claim 1 1-ethyl-5-(2-ethyl-2,3-dihydro-1H-inden-2-yl)-1H-imidazole or a non-toxic, pharmaceutically acceptable salts.

8. A compound according to claim 1 4-(2-ethyl-2,3-dihydro-1H-inden-2-yl)-1-n-propyl-1H-imidazole or a non-toxic, pharmaceutically acceptable salts.

9. A compound according to claim 1 5-(2-ethyl-2,3-dihydro-1H-inden-2-yl)-1-n-propyl-1H-imidazole or a non-toxic, pharmaceutically acceptable salt thereof.

10. A compound according to claim 1 1-benzyl-4-(2-ethyl-2,3-dihydro-1H-inden-2-yl)-1H-imidazole or a non-toxic, pharmaceutically acceptable salt thereof.

11. A compound according to claim 1 1-benzyl-5-(2-ethyl-2,3-dihydro-1H-inden-2-yl)-1H-imidazole or a non-toxic, pharmaceutically acceptable salt thereof.

12. A compound according to claim 1 2-ethyl-2-(1-methyl-1H-imidazol-4-yl)-1-indanone or a non-toxic, pharmaceutically acceptable salt thereof.

13. A compound according to claim 1 2-ethyl-2-(1-methyl-1H-imidazole-5-yl)-1-indanone or a non-toxic, pharmaceutically acceptable salt thereof.

14. A compound according to claim 1 [2,3-dihydro-2-(1-methyl-1H-imidazole-4-yl)-1H-inden-2-yl]-methanol or a non-toxic, pharmaceutically acceptable salt thereof.

15. A compound according to claim 1 4-(2,3-dihydro-2-methoxymethyl-1H-inden-2-yl)-1-methyl-1H-imidazole or a non-toxic, pharmaceutically acceptable salt thereof.

16. A compound according to claim 1 [2-(1-benzyl-1H-imidazole-4-yl)-2,3-dihydro-1H-inden-2-yl]-methanol or a non-toxic, pharmaceutically acceptable salt thereof.

17. A compound according to claim 1 1-benzyl-4-(2,3-dihydro-2-methoxymethyl-1H-inden-2-yl)-1H-imidazole or a non-toxic, pharmaceutically acceptable salt thereof.

18. A compound according to claim 1 4-(2,3-dihydro-2-methoxymethyl-1H-inden-2-yl)-1H-imidazole or a non-toxic, pharmaceutically acceptable salt thereof.

19. A compound according to claim 1 2-ethyl-2-[1-(4-chlorobenzyl)-1H-imidazol-4-yl]-1-indanone or a non-toxic, pharmaceutically acceptable salt thereof.

20. A compound according to claim 1 2-(1-methyl-1H-imidazol-4-yl]-2-n-propyl-1-indanone or a non-toxic, pharmaceutically acceptable salt thereof.

21. A compound according to claim 1 2-(1-methyl-1H-imidazol-5-yl]-2-n-propyl-1-indanone or a non-toxic, pharmaceutically acceptable salt thereof.

22. A compound according to claim 1 2-(1-ethyl-1H-imidazol-4-yl]-2-n-propyl-1-indanone or a non-toxic, pharmaceutically acceptable salt thereof.

23. A compound according to claim 1 2-(1-ethyl-1H-imidazol-5-yl]-2-n-propyl-1-indanone or a non-toxic, pharmaceutically acceptable salt thereof.

24. A compound according to claim 1 1-ethyl-4-(2,3-dihydro-2-n-propyl-1H-inden-2-yl)-1H-imidazole or a non-toxic, pharmaceutically acceptable salt thereof.

25. A compound according to claim 1 4-(2,3-dihydro-2-n-propyl-1H-inden-2-yl)-1-methyl-1H-imidazole or a non-toxic, pharmaceutically acceptable salt thereof.

26. A compound according to claim 1 [2-(1-ethyl-1H-imidazol-4-yl)-2,3-dihydro-1H-inden-2-yl]methanol or a non-toxic, pharmaceutically acceptable salt thereof.

27. A compound according to claim 1 1-ethyl-4-(2,3-dihydro-2-methoxymethyl-1H-inden-2-yl)-1H-imidazole or a non-toxic, pharmaceutically acceptable salt thereof.

28. A compound according to claim 1 2-ethyl-2-(1-ethyl-1H-imidazol-4-yl)-1-indanone or a non-toxic, pharmaceutically acceptable salt thereof.

29. An α-receptor antagonizing composition comprising a compound as claimed in claim 1 in association with a compatible, pharmaceutically acceptable carrier.

30. A method of antagonising α$_2$-receptors in a subject in whom such antagonism is desired, comprising administering to the subject an amount of a compound according to claim 1 effective to achieve the desired level of α$_2$-receptor antagonism.

* * * * *